United States Patent [19]
Phan et al.

[11] Patent Number: 5,874,614
[45] Date of Patent: Feb. 23, 1999

[54] SODIUM (S)-2-(6-METHOXY-2-NAPHTHYL) PROPIONATE MONOHYDRATE

[75] Inventors: Hao V. Phan, Columbia, S.C.; Robert H. Allen, Baton Rouge, La.; Richard A. Coats, Cope, S.C.

[73] Assignee: Albemarle Corporation, Richmond, Va.

[21] Appl. No.: 988,969

[22] Filed: Dec. 11, 1997

[51] Int. Cl.[6] .................................................. C07C 63/34
[52] U.S. Cl. ........................................ 562/467; 562/466
[58] Field of Search ..................... 562/467, 466

[56] References Cited

U.S. PATENT DOCUMENTS

| | | | |
|---|---|---|---|
| 3,228,831 | 1/1966 | Nicholson et al. | 167/53 |
| 3,385,886 | 5/1968 | Nicholson et al. | 260/515 |
| 3,562,336 | 2/1971 | Nelson | 260/613 |
| 3,651,106 | 3/1972 | Harrison | 260/429 R |
| 3,651,149 | 3/1972 | Harrison | 260/606.5 B |
| 3,652,683 | 3/1972 | Harrison | 260/612 D |
| 3,683,015 | 8/1972 | Dyson | 260/520 |
| 3,686,183 | 8/1972 | Dyson | 260/284 |
| 3,828,033 | 8/1974 | Nelson | 260/240 R |
| 3,904,682 | 9/1975 | Fried et al. | 260/520 |
| 3,904,683 | 9/1975 | Day et al. | 260/520 |
| 3,959,364 | 5/1976 | Armitage et al. | 260/515 R |
| 3,975,432 | 8/1976 | Alvarez | 260/520 R |
| 3,978,116 | 8/1976 | Fried et al. | 260/500.5 H |
| 3,988,365 | 10/1976 | Gallegra | 260/520 D |
| 4,001,301 | 1/1977 | Fried et al. | 260/473 F |
| 4,009,197 | 2/1977 | Fried et al. | 260/473 F |
| 4,239,914 | 12/1980 | Campolmi et al. | 562/466 |
| 4,245,121 | 1/1981 | Ohno et al. | 562/401 |
| 4,246,164 | 1/1981 | Felder et al. | 260/501.17 |
| 4,246,193 | 1/1981 | Holton | 260/501.17 |
| 4,395,571 | 7/1983 | Dvorak | 562/466 |
| 4,571,333 | 2/1986 | Hsiao et al. | 424/22 |
| 4,605,758 | 8/1986 | Schloemer | 562/418 |
| 4,609,766 | 9/1986 | Giordano et al. | 568/592 |
| 4,621,152 | 11/1986 | Bemini | 562/401 |
| 4,623,736 | 11/1986 | Walker et al. | 549/369 |
| 4,654,438 | 3/1987 | Schloemer | 562/496 |
| 4,723,033 | 2/1988 | Erickson | 560/56 |
| 4,803,079 | 2/1989 | Hsiao et al. | 424/468 |
| 4,851,444 | 7/1989 | Sunshine et al. | 514/570 |
| 4,857,462 | 8/1989 | Maier et al. | 435/197 |
| 4,864,063 | 9/1989 | Piccolo et al. | 568/328 |
| 4,877,620 | 10/1989 | Loew et al. | 424/451 |
| 5,015,764 | 5/1991 | Manimaran et al. | 562/401 |
| 5,034,416 | 7/1991 | Smith | 514/568 |
| 5,220,053 | 6/1993 | Choudhury et al. | 562/401 |
| 5,221,765 | 6/1993 | Patil et al. | 562/401 |
| 5,235,095 | 8/1993 | Kadkhodayan et al. | 560/218 |
| 5,235,100 | 8/1993 | Choudhury et al. | 562/401 |
| 5,235,101 | 8/1993 | Patil et al. | 562/401 |
| 5,248,813 | 9/1993 | Manimaran et al. | 562/401 |
| 5,256,816 | 10/1993 | Murray et al. | 562/401 |
| 5,278,337 | 1/1994 | Manimaran et al. | 562/401 |
| 5,278,338 | 1/1994 | Trace | 562/401 |
| 5,574,183 | 11/1996 | Patil et al. | 562/401 |

*Primary Examiner*—Paul J. Killos
*Attorney, Agent, or Firm*—Philip M. Pippenger

[57] ABSTRACT

Novel and very useful forms of sodium (S)-2-(6-methoxy-2-naphthyl)propionate are provided. These forms are sodium (S)-2-(6-methoxy-2-naphthyl)propionate monohydrate having an average particle size significantly larger than about 70 microns—the size of conventional sodium (S)-2-(6-methoxy-2-naphthyl)propionate—and a chiral purity of at least 98% (S)-enantiomer. Process technology enabling the production of such novel products is also described. The provision of such novel products makes possible significant improvements in processing time, plant capacity and product handling operations.

29 Claims, No Drawings

SODIUM (S)-2-(6-METHOXY-2-NAPHTHYL) PROPIONATE MONOHYDRATE

BACKGROUND

The sodium salt of (S)-2-(6-methoxy-2-naphthyl) propionic acid is a commercially available anti-inflammatory agent with the generic name of naproxen sodium.

A process used for the production of naproxen sodium involves reacting (S)-2-(6-methoxy-2-naphthyl)propionic acid dissolved in toluene with an aqueous sodium hydroxide solution, with subsequent removal of water by heating the slurry to an ending temperature of 100° C. and a pressure of 1 atmosphere. The resultant anhydrous naproxen sodium has an average particle size in the range of about 30 to about 70 microns, and is in the form of small needle-like particles typically having an aspect ratio of about 10, with the length being approximately 200 to 300 microns and the width ranging from about 15 to about 45 microns. To achieve the required high chiral purity naproxen sodium (99% minimum), it has been necessary to use long cycle times and to form and use (S)-2-(6-methoxy-2-naphthyl)propionic acid of relatively high chiral purity (97% minimum).

A highly desirable contribution to the art would be the provision of forms of sodium (S)-2-(6-methoxy-2-naphthyl) propionate having an average particle size significantly larger than about 70 microns, especially if such material could have a chiral purity of at least 98% (S)-enantiomer, and a process technology enabling the production of such material. The achievement of these objectives would be of inestimable value from the standpoints, inter alia, of processing time, plant capacity and product handling operations.

This invention is deemed to constitute such a contribution to the art, as it enables the achievement of the foregoing objectives.

THE INVENTION

Provided by this invention as a new composition of matter is sodium (S)-2-(6 -methoxy-2-naphthyl)propionate monohydrate having an average particle size of at least about 120 microns, and a chiral purity of at least 98 wt % (S)-enantiomer, and preferably at least 99 wt % (S)-enantiomer. In preferred embodiments the sodium (S)-2-(6-methoxy-2-naphthyl)propionate monohydrate has an average particle size of at least about 250 microns, and most preferably its particle size is at least about 330 microns.

In additional embodiments, this invention provides process technology for producing such new compositions of matter. One such process comprises a) forming concurrently or in any sequence a solids-free liquid mixture from (i) (S)-2-(6-methoxy-2-naphthyl) propionic acid having a chiral purity of at least about 82%, but below 99%, and preferably having a chiral purity of at least about 91%, but below 98%, (ii) water, (iii) at least one water-soluble inorganic basic sodium compound (e.g., sodium hydroxide and/or sodium oxide) in an amount proportioned to neutralize from about 50 to about 97% of said acid, and (iv) an innocuous organic solvent; and b) removing water from said mixture by distillation such that a pot residue containing sodium (S)-2-(6-methoxy-2-naphthyl)propionate monohydrate having an average particle size of at least about 120 microns, and a chiral purity of at least 98% (S)-enantiomer is formed.

In preferred process embodiments, the organic solvent used is a solvent that can form an azeotrope with water that boils below 100° C. at ambient pressure.

Among the advantages of this invention is the fact that it enables use in the process of (S)-2-(6-methoxy-2-naphthyl) propionic acid of lower chiral purity than the desired sodium (S)-2-(6-methoxy-2-naphthyl)propionate monohydrate to be produced. This in turn results in a significant plant capacity increase, especially in a prior resolution step leading to the formation of the (S)-2-(6-methoxy-2-naphthyl)propionic acid being formed and used as the starting material in the present process. Another important advantage is that the process enables a substantial reduction in cycle time. Instead of slow feed of sodium hydroxide solution to the initial 2-(6-methoxy-2-naphthyl)propionic acid followed by a slow water strip, these steps can be conducted much more rapidly. For example, a 50% aqueous NaOH solution can be charged in minutes, with water subsequently added (also in minutes) to achieve total dissolution of the sodium (S)-2-(6-methoxy-2-naphthyl)propionate prior to commencement of water removal by distillation. Centrifugation cycle time can also be dramatically reduced, because of the much larger particle sizes of the sodium (S)-2-(6-methoxy-2-naphthyl) propionate formed, and its ability to dewater more efficiently. Also product handling is simplified in various operations such as drying, flowing, screening, or tableting.

This invention also provides as a new composition of matter anhydrous sodium (S)-2-(6-methoxy-2-naphthyl) propionate having an average particle size of at least about 120 microns, and a chiral purity of at least 98% (S)-enantiomer, and preferably at least 99% (S)-enantiomer. In preferred embodiments the anhydrous sodium (S)-2-(6-methoxy-2-naphthyl)propionate has an average particle size of at least about 250 microns, and most preferably its particle size is at least about 330 microns. Still another embodiment of this invention is a process for producing these various anhydrous salts of this invention, which process comprises dehydrating particulate sodium (S)-2-(6-methoxy-2-naphthyl)propionate monohydrate having an average particle size of at least about 120 microns, and a chiral purity of at least 98% (S)-enantiomer, and preferably at least 99% (S)-enantiomer, under conditions effective to form, and so that there is formed, particulate anhydrous sodium (S)-2-(6-methoxy-2-naphthyl)propionate having an average particle size of at least about 120 microns, and a chiral purity, respectively, of at least 98% (S)-enantiomer, and preferably at least 99% (S)-enantiomer. In preferred embodiments the sodium (S)-2-(6-methoxy-2-naphthyl) propionate monohydrate and the anhydrous sodium (S)-2-(6-methoxy-2-naphthyl)propionate both have an average particle size of at least about 250 microns, and most preferably both have an average particle size of at least about 330 microns. The special particle size and chiral purity characteristics of the anhydrous sodium (S)-2-(6-methoxy-2-naphthyl)propionates of this invention make possible simplified and facilitated product handling in various operations such as drying, flowing, screening, or tableting, while maintaining the high pharmacological activity of the product.

Among the advantages of the dehydration process of this invention is that when properly carried out (e.g., as described in the Examples hereinafter), the average particle size and the chiral purity of the resultant anhydrous salt are essentially the same as the average particle size and the chiral purity of the monohydrate salt as formed in accordance with this invention.

Other embodiments, advantages and features of this invention will become still further apparent from the ensuing description and appended claims.

Step a)

In conducting step a) above, ingredients (i), (ii), (iii), and (iv) can be charged to the reaction vessel concurrently or in any sequence, or they can in part be charged concurrently and also in part charged in one or more sequences. Moreover, these ingredients can be charged as individual ingredients, or they can be charged as one or more preformed subcombinations, such as by charging a preformed solution made from all or a portion of ingredients (i) and (iv) and/or a preformed solution made from all or a portion of ingredients (ii) and (iii), and if both of these preformed solutions are used, they can be charged to the reaction vessel concurrently and/or sequentially in any order. It will of course be understood by those skilled in the chemical arts that on mixing water-soluble inorganic sodium compounds such as sodium hydroxide with water, ionization takes place in the solution such that it contains sodium cations and anions from the compound used, e.g., hydroxyl anions in the case of sodium hydroxide. Moreover, chemists know that upon mixing sodium oxide with water, an ionized solution of sodium hydroxide is formed. In short, sodium hydroxide and sodium oxide form the same kind of aqueous solutions.

Suitable water-soluble inorganic basic sodium compounds that can be used in step a) of the process include, for example, sodium hydroxide, sodium oxide, sodium carbonate, sodium bicarbonate, sodium amide, and similar water-soluble basic inorganic sodium compounds, whether used singly or in combinations of two or more such compounds. In theory, sodium cyanide can be used, but this is not recommended because of the formation of hydrogen cyanide, especially on acidification. The sodium compounds can be used either in anhydrous or hydrated forms, where such exist. Metallic sodium could be used to generate the sodium hydroxide in situ, but for reasons of safety, this is not recommended.

Preferably, the water-soluble inorganic basic sodium compound or mixture thereof is added to the reaction vessel as a solids-free preformed aqueous solution. In any event, the resulting mixture formed in a) should contain enough water to totally solubilize all of the sodium (S)-2-(6-methoxy-2-naphthyl)propionate before distillation.

When conducting step a) it is important to make sure that initially there are no visually perceptible solids present, i.e., the mixture when in static condition (i.e. when not being stirred or otherwise agitated) should be visually clear, indicating that everything is in solution. In short, the mixture should be solids-free at the outset. By conducting the neutralization reaction in step a) with everything in the liquid phase ensures that the sodium (S)-2-(6-methoxy-2-naphthyl)propionate monohydrate which separates during the water removal distillation in step b) will achieve the requisite high chiral purity. In many cases the mixture in step a) will be a two-phase mixture of organic solvent and water, but it is possible to have a homogeneous one-phase mixture of the organic solvent and water. In either case, the important thing is that there initially be no visually perceptible amount of solids present in the mixture when the distillation of step b) is started. Of course, it would not be disastrous if a few miniscule specks of non-toxic, harmless solids are present at the outset of the distillation, but of course such specks may remain and constitute a trace amount of unwanted impurities in the end product.

Step a) is conveniently initiated at ambient room temperature and in such case a slight temperature increase is often experienced due to the exothermic character of the neutralization reaction. However step a) can be conducted at any temperature in the range of about 0° C. (provided the water is in the liquid state) to about 94° C.

Suitable innocuous organic solvents which may be used in the process include, for example, such substances as propionitrile, butyronitrile, isobutyronitrile, 2-butenone, 1,4-dioxane, isobutyl nitrate, pyridine, 3-pentanone, butyl formate, propyl acetate, piperidine, 3,3-dimethyl-2-butanone, amyl formate, butyl acetate, propyl propionate, tert-amyl ethyl ether, isobutyl ether, benzene, toluene, and similar solvents. Hydrocarbon solvents are preferred, especially hydrocarbon solvents that can form an azeotrope with water that boils below 100° C. at ambient pressure. The term "innocuous" is employed in the sense that the organic solvent either is inert or it is a substance that causes no material interference with the process if is not truly inert. Thus a solvent such as pyridine is capable of reacting with (S)-2-(6-methoxy-2-naphthyl)propionic acid to form an amine salt. However if used with a stronger basic sodium compound, sodium (S)-2-(6-methoxy-2-naphthyl) propionate will be formed, and thus the pyridine is innocuous albeit not inert, and thus can be used as the solvent. Preferred solvents are those that are inert under the conditions and in the environment employed.

The distillation in step b) should be conducted such that a mother liquor containing sodium (S)-2-(6-methoxy-2-naphthyl)propionate monohydrate remains in the distillation vessel. The sodium (S)-2-(6-methoxy-2-naphthyl) propionate monohydrate can then be recovered by a suitable procedure such as draining, decantation, filtration, centrifugation, or the like, and impurities can be removed by washing the product with a suitable organic substance such as toluene. The separation and recovery of the solids from the pot residue is preferably carried out by centrifuging the pot residue remaining after the distillation, although other suitable methods of solids-liquid separation may be used. During this separation and recovery step two conditions should be observed and maintained to avoid contamination of the sodium (S)-2-(6-methoxy-2-naphthyl)propionate product being recovered. First, the temperature of the pot residue from which the solid, high chiral purity sodium (S)-2-(6-methoxy-2-naphthyl)propionate product is being separated should be kept high enough to keep in solution the low chiral purity sodium (S)-2-(6-methoxy-2-naphthyl) propionate that is already in solution in the organic solvent. Secondly, the unreacted excess of (S)-2-(6-methoxy-2-naphthyl)propionic acid present in the pot residue should also be kept dissolved in the organic solvent. These two conditions can best be accomplished by centrifuging the pot residue at a temperature sufficiently high to keep both the low chiral purity sodium (S)-2-(6-methoxy-2-naphthyl) propionate and the free acid in solution in the organic solvent. The temperature used will depend on the organic solvent used and the relative proportions of organic solvent, low chiral purity sodium (S)-2-(6-methoxy-2-naphthyl) propionate, and free (S)-2-(6-methoxy-2-naphthyl) propionic acid. Thus in any given situation it is desirable to conduct a few simple laboratory experiments to measure (a) the solubility of several samples of sodium (S)-2-(6-methoxy-2-naphthyl)propionate of different known low chiral purities in the particular solvent at several appropriate temperatures, and (b) the solubility of the (S)-2-(6-methoxy-2-naphthyl)propionic acid in the particular solvent at several appropriate temperatures. From this information one can ascertain the amount of the particular organic solvent to be used and the temperature to be used with the projected amounts of low chiral purity sodium (S)-2-(6-methoxy-2-naphthyl)propionate and of the free (i.e., unneutralized or excess) (S)-2-(6-methoxy-2-naphthyl)propionic acid that is to be present in the pot residue. As an example, when using toluene or other higher boiling liquid aromatic hydrocarbons as the organic solvent, the foregoing two conditions can be satisfied by keeping the temperature of the pot residue at about 60° C. or above (e.g., 60° to 90° C.) during centrifugation. After its recovery, the product is then dried preferably at ambient temperature under reduced pressure to remove residual organic solvent. It can then be further purified by recrystallization, if desired.

To produce the anhydrous sodium (S)-2-(6-methoxy-2-naphthyl)propionate of this invention from the sodium (S)-2-(6-methoxy-2-naphthyl)propionate monohydrate, a suitable dehydration process is employed. At least two different dehydration procedures are highly suitable for use in such process. In accordance with one such procedure, particulate sodium (S)-2-(6-methoxy-2-naphthyl)propionate monohydrate having an average particle size of at least about 120 microns, and a chiral purity of at least 98% (S)-enantiomer is heated at one or more temperatures of at least about 25° C., preferably under reduced pressure, for a period of time sufficient to remove water of hydration from the particulate solids and thereby form particulate anhydrous sodium (S)-2-(6-methoxy-2-naphthyl)propionate having an average particle size of at least about 120 microns, and a chiral purity of at least 98% (S)-enantiomer. In general, the lower the pressure, the shorter the drying time, and thus any reduced pressure that can be achieved on a practical and cost-effective basis can be used. Such reduced pressure dehydration procedures are the preferred procedures. Another suitable procedure comprises heating a slurry of particulate sodium (S)-2-(6-methoxy-2-naphthyl)propionate monohydrate having an average particle size of at least about 120 microns, and a chiral purity of at least 98% (S)-enantiomer in an inert liquid organic medium at one or more temperatures of at least about 50° C., preferably under reduced pressure for a period of time sufficient to remove water of hydration from the particulate solids and thereby form a slurry of particulate anhydrous sodium (S)-2-(6-methoxy-2-naphthyl)propionate having an average particle size of at least about 120 microns, and a chiral purity of at least 98% (S)-enantiomer and then recovering the particulate product from the slurry such as by decantation, filtration, centrifugation, or like separation procedure. Thereafter, the recovered product can be subjected to drying and purification procedures, if desired. In either such procedure the conditions used, especially the temperature and time of heating, should be controlled so as not to melt or otherwise materially interfere with the size and shape of the particulate anhydrous product. Thus temperatures to which the product is exposed during the dehydration procedure (and during subsequent drying and purification steps, if used) are typically kept below about 245° C.

When effecting the dehydration using the above slurry procedure, inert solvents in which sodium (S)-2-(6-methoxy-2-naphthyl)propionate monohydrate and anhydrous sodium (S)-2-(6-methoxy-2-naphthyl)propionate are essentially insoluble can be used in forming the slurry of particulate sodium (S)-2-(6-methoxy-2-naphthyl)propionate monohydrate. Suitable solvents that have such properties are included among such liquid organic diluents as nitriles, ketones, ethers, esters, and/or hydrocarbons. Of these aromatic hydrocarbons such as benzene, toluene, one or more xylenes, ethylbenzene, etc., are preferred.

When it is desired to form the anhydrous sodium (S)-2-(6-methoxy-2-naphthyl)propionate of this invention, the dehydration process is conducted as a separate operation in order to ensure formation of product having the desired shape and size.

To determine average particle size, various known procedures can be used. One preferred procedure involves forming a dispersion of a small sample (e.g., 0.04–0.06 gram) of the sodium (S)-2-(6-methoxy-2-naphthyl)propionate in about 200 mL of a suitable medium such as a 0.1% solution of Aerosol OT in Isopar-G. Particle size is then measured using a suitably calibrated laser scattering particle size distribution analyzer, such as a Horiba LA-900 or LA-910 particle size distribution analyzer.

Chiral purity of sodium (S)-2-(6-methoxy-2-naphthyl)propionate can be determined by use of the procedure of Hermansson and Erikson, entitled "Direct Liquid Chromatographic Resolution of Acidic Drugs Using A Chiral Alpha-Acid Glycoprotein Column" and appearing in *Journal of Liquid Chromatography*, 1986, 9(2&3), 621–639, with the following slight modifications:

Flow: 1.2 mL/min.

Detection: 225 nm

Injection volume: 1 μL

Sample concentration: 300 ppm dissolved in the mobile phase.

Column: Chiral AGP100-4 (alpha-glycoprotein) 4×100 mm (available from Advanced Separation Technologies).

The following Examples are presented in order to illustrate the practice and advantages of the invention. The Examples are not intended to constitute limitations on the invention.

COMPARATIVE EXAMPLE A

The following were charged to a 1000-mL, 3-neck reactor equipped with a mechanical agitator, an adaptor fitted with a thermometer and a condenser: 72.56 grams of 2-(6-methoxy-2-naphthyl)propionic acid assaying 98.91% S-enantiomer, 25.22 grams of 2-(6-methoxy-2-naphthyl)propionic acid assaying 99.70% S-enantiomer, and 2.29 grams of racemic 2-(6-methoxy-2-naphthyl)propionic acid, 464.48 grams of fresh toluene, and 1.50 grams of water. The mixture was heated to 85° C. to dissolve the solids. A total of 31.29 grams of 50.03 wt % NaOH was then fed over 61 minutes. The thin slurry was agitated at 85° C. for 10 minutes and then water was stripped to 94° C. in 102 minutes. Totals of 15.20 grams of water and 7.48 grams of toluene were collected during this strip. The slurry was refluxed for 124 minutes. Water strip was resumed and continued until the temperature reached 100° C., which took a total of 109 minutes. The total amount of water collected during this second strip was 7.51 grams and the amount of toluene removed was 14.31 grams. The batch was agitated at 100° C. for 15 minutes and then cooled to 65° C. in 60 minutes. It was centrifuged immediately upon reaching 65° C. The centrifuge cake was washed with 204.65 grams of warm (65° C.) toluene. Totals of 399.36 and 192.16 grams of mother liquor and wash liquor were recovered, respectively. The wet centrifuge cake weighed 103.45 grams which after drying for 12 hours at 80°–90° C. and under full vacuum yielded 91.90 grams of dry final product. Chiral purities for the product and the mother liquor were found by analysis to be 98.96% S-enantiomer and 92.44% S-enantiomer, respectively.

EXAMPLE 1

The following were charged to the same reactor setup as in the above Comparative Example: 95.90 grams of 2-(6-methoxy-2-naphthyl)propionic acid assaying 99.60%

S-enantiomer, 5.68 grams of racemic 2-(6-methoxy-2-naphthyl)propionic acid, 461.58 grams of fresh toluene, and 1.70 grams of water. The mixture was heated to 80° C. to dissolve. The composite solution was analyzed for chiral purity (result: 96.80% S-enantiomer). A total of 31.87 grams of 49.93 wt % NaOH was then fed over 60 minutes. The thin slurry was agitated at 85° C. for 10 minutes and then water was stripped to 94° C. in 212 minutes. The total amount of water collected during the strip was 15.72 grams and the amount of toluene removed was 8.67 grams. The batch was agitated at 93.8°–94.3° C. for 15 minutes and cooled to 65° C. in 122 minutes. It was centrifuged after aging at 65° C. for 30 minutes and the centrifuge cake (sodium (S)-2-(6-methoxy-2-naphthyl)propionate monohydrate) was washed with 195.69 grams of water (65° C.) toluene. Totals of 407.85 and 180.41 grams of mother liquor and wash liquor were recovered, respectively. The wet centrifuge cake weighed 109.56 grams which after drying for 7.5 hours at 80°–90° C. and under full vacuum yielded 91.18 grams of dry final product (anhydrous sodium (S)-2-(6-methoxy-2-naphthyl)propionate). Also left in the reactor were about 2 grams of solids. Chiral purities for the product and the mother liquor were found by analysis to be 98.85% S-enantiomer and 86.50% S-enantiomer, respectively.

EXAMPLE 2

The following were charged to the same reactor setup as in the above Comparative Example: 95.95 grams of 2-(6-methoxy-2-naphthyl)propionic acid assaying 99.60% S-enantiomer, 5.63 grams of racemic 2-(6-methoxy-2-naphthyl)propionic acid, 461.15 grams of fresh toluene, and 1.65 grams of water. The mixture was heated to 85° C. to dissolve the solids. The composite solution was analyzed for chiral purity (result: 96.80% S-enantiomer). A total of 31.56 grams of 49.93 wt % NaOH was added over 3 minutes. Water (16.04 grams) was then added slowly in 20 minutes. Two liquid phases were obtained, with no solids apparent. Water was stripped to 93.7° C. in 354 minutes. The total amount of water collected during the strip was 31.15 grams and the amount of toluene removed was 14.62 grams. The batch was agitated at 93.7°–94.1° C. for 15 minutes and cooled to 65° C. in 120 minutes. It was centrifuged after aging at 65° C. for 30 minutes and the centrifuge cake (sodium (S)-2-(6-methoxy-2-naphthyl)propionate monohydrate) was washed with 194.20 grams of warm (65° C.) toluene. Totals of 433.18 and 169.27 grams of mother liquor and wash liquor were recovered, respectively. The wet centrifuge cake weighed 100.89 grams which after drying for 10 hours at ambient temperature and under full vacuum yielded 99.10 grams of dry product. The product was dried further for 4 hours at 80°–90° C. and under full vacuum yielded 87.05 grams of dry final product (anhydrous sodium (S)-2-(6-methoxy-2-naphthyl)propionate). Chiral purities for the product and the mother liquor were found by analysis to be 99.53% S-enantiomer and 82.36% S-enantiomer, respectively.

EXAMPLE 3

The following were charged to the same reactor setup as in the above Comparative Example: 104.50 grams of 2-(6-methoxy-2-naphthyl)propionic acid assaying 99.60% S-enantiomer, 18.97 grams of racemic 2-(6-methoxy-2-naphthyl)propionic acid, 561.20 grams of fresh toluene, and 2.00 grams of water. The mixture was heated to 80° C. to dissolve. The composite solution was analyzed for chiral purity (result: 91.95% S-enantiomer). A total of 34.40 grams of 50.05 wt % NaOH was then added over 3 minutes. Water (14.13 grams) was added. Two clear liquid phases were obtained. Water was stripped to 93.8° C. in 713 minutes. The total amount of water collected during the strip was 31.51 grams and the amount of toluene removed was 9.35 grams. The batch was agitated at 93.8°–94.3° C. for 15 minutes and cooled to 65° C. in 120 minutes. When the temperature reached about 70° C., the slurry thickened, with the mother liquor very cloudy. The slurry was reheated to 73° C. and was aged overnight. It was heated further to 76° C. and then agitated for 4 hours. It was then centrifuged and the centrifuge cake (sodium (S)-2-(6-methoxy-2-naphthyl)propionate monohydrate) was washed with 199.60 grams of warm (75° C.) toluene. Totals of 541.01 and 148.86 grams of mother liquor and wash liquor were recovered, respectively. The wet centrifuge cake weighed 99.90 grams which after drying for 6 hours at ambient temperature and under full vacuum yielded 92.00 grams of dry product. The product was dried further for 5 hours at 80°–90° C. and under full vacuum yielded 85.65 grams of dry final product (anhydrous sodium (S)-2-(6-methoxy-2-naphthyl)propionate). Chiral purities for the product and the mother liquor were found by analysis to be 98.36% S-enantiomer and 80.75% S-enantiomer, respectively.

EXAMPLE 4

The following were charged to the same reactor setup as in the above Comparative Example: 41.81 grams of 2-(6-methoxy-2-naphthyl)propionic acid assaying 99.60% S-enantiomer, 28.40 grams of 2-(6-methoxy-2-naphthyl)propionic acid assaying 99.68% S-enantiomer, 34.40 grams of 2-(6-methoxy-2-naphthyl)propionic acid assaying 99.10% S-enantiomer, 18.62 grams of racemic 2-(6-methoxy-2-naphthyl)propionic acid, 561.34 grams of fresh toluene, and 1.81 grams of water. The mixture was heated to 85° C. to dissolve. The composite solution was analyzed for chiral purity (result: 92.16% S-enantiomer). A total of 32.22 grams of 50.05 wt % NaOH was then added over 3 minutes. Water (8.46 grams) was added. Two clear liquid phases were obtained. Water was stripped to 94.0° C. in 593 minutes. The total amount of water collected during the strip was 24.11 grams and the amount of toluene removed was 8.62 grams. The batch was agitated at 94.0°–94.2° C. for 15 minutes and cooled to 70° C. in 120 minutes and then aged for 30 minutes. Solids in the slurry settled well, and the mother liquor was very clear and transparent. It was then centrifuged and the centrifuge cake (sodium (S)-2-(6-methoxy-2-naphthyl)propionate monohydrate) was washed with 196.75 grams of warm (70° C.) toluene. Totals of 563.79 and 171.53 grams of mother liquor and wash liquor were recovered, respectively. The wet centrifuge cake weighed 87.80 grams which after drying for 6 hours at ambient temperature and under full vacuum yielded 83.70 grams of dry product. The product was dried further for 4 hours at 80°–90° C. and under full vacuum, and this yielded 78.02 grams of dry final product (anhydrous sodium (S)-2-(6-methoxy-2-naphthyl) propionate). Chiral purities for the product and the mother liquor were found by analysis to be 99.24% S-enantiomer and 81.65% S-enantiomer, respectively.

EXAMPLE 5

The following were charged to the same reactor setup as in the above Comparative Example: 105.29 grams of 2-(6-methoxy-2-naphthyl)propionic acid assaying 99.17% S-enantiomer, 18.15 grams of racemic 2-(6-methoxy-2-naphthyl)propionic acid, 559.77 grams of fresh toluene, and 1.73 grams of water. The mixture was heated to 85° C. to dissolve the solids. The composite solution was analyzed for chiral purity (result: 92.12% S-enantiomer). A total of 32.20 grams of 50.05 wt % NaOH was then added over 3 minutes. Water (8.55 grams) was added. Two clear liquid phases were obtained. Water was stripped to 93.7° C. in 396 minutes. The total amount of water collected during the strip was 24.08 grams and the amount of toluene removed was 9.93 grams. The batch was agitated at 93.7°–94.2° C. for 15 minutes and cooled to 70° C. in 135 minutes and agitated for 90 minutes. Solids in the slurry initially settled well, but 60 minutes into the 70° C. ride, it began thickening and the mother liquor became very cloudy. It was then centrifuged after riding at 70° C. for a total of 90 minutes. The centrifuge cake (sodium (S)-2-(6-methoxy-2-naphthyl)propionate monohydrate) was washed with 202.07 grams of warm (70° C.) toluene. Totals of 548.36 and 175.09 grams of mother liquor and wash liquor were recovered, respectively. The wet centrifuge cake weighed 94.33 grams which after drying for 8 hours at ambient temperature and under full vacuum yielded 85.84 grams of product. The product was dried further for 4 hours at 80°–90° C. and under full vacuum yielding 80.15 grams of dry final product (anhydrous sodium (S)-2-(6-methoxy-2-naphthyl)propionate). Chiral purities for the product and the mother liquor were found by analysis to be 98.36% S-enantiomer and 83.21% S-enantiomer, respectively.

EXAMPLE 6

The following were charged to the same reactor setup as in the above Comparative Example: 105.52 grams of 2-(6-methoxy-2-naphthyl)propionic acid assaying 99.17% S-enantiomer, 18.20 grams of racemic 2-(6-methoxy-2-naphthyl)propionic acid, 568.22 grams of fresh toluene, and 1.82 grams of water. The mixture was heated to 85° C. to dissolve the solids. The composite solution was analyzed for chiral purity (result: 92.10% S-enantiomer). A total of 32.24 grams of 49.99 wt % NaOH was then added. Water (8.54 grams) was also added. Two clear liquid phases were obtained. Water was stripped to 93.8° C. in 538 minutes. The total amount of water collected during the strip was 23.08 grams and the amount of toluene removed was 10.95 grams. The batch was agitated at 93.8°–94.1° C. for 15 minutes and cooled to 75° C. in 63 minutes. It was then held at 75° C. for 120 minutes. Solids in the slurry settled well throughout the two-hour 75° C. ride. The centrifuge cake (sodium (S)-2-(6-methoxy-2-naphthyl)propionate monohydrate) was washed with 196.30 grams of hot (75° C.) toluene. Totals of 571.50 and 171.38 grams of mother liquor and wash liquor were recovered, respectively. The wet centrifuge cake weighed 84.22 grams which after drying for 12 hours at ambient temperature and under full vacuum yielded 81.05 grams of product. The product was dried further for 3 hours at 80°–90° C. and under full vacuum, with 75.76 grams of dry final product (anhydrous sodium (S)-2-(6-methoxy-2-naphthyl)propionate) obtained. Chiral purities for the product and the mother liquor were found by analysis to be 99.17% S-enantiomer and 82.36% S-enantiomer, respectively.

EXAMPLE 7

The following were charged to a 12-liter, jacketed, and 3-neck reactor equipped with a mechanical agitator, a thermometer, and a condenser: 500.47 grams of 2-(6-methoxy-2-naphthyl)propionic acid assaying 88.10% S-enantiomer, 649.33 grams of 2-(6-methoxy-2-naphthyl) propionic acid assaying 99.17% S-enantiomer, 224.87 grams of 2-(6-methoxy-2-naphthyl)propionic acid assaying 99.57% S-enantiomer, 105.06 grams of racemic 2-(6-methoxy-2-naphthyl)propionic acid, 6744.25 grams of fresh toluene, and 21.64 grams of water. The mixture was heated to 85° C. to dissolve the solids. The composite solution was analyzed for chiral purity (result: 91.95% S-enantiomer). A total of 391.73 grams of 49.22 wt % NaOH was then added with the temperature being maintained below 87.5° C. Water (102.06 grams) was also added. Two clear liquid phases were obtained. Water was stripped to 94.0° C. in 369 minutes. The total amount of water collected during the strip was 293.90 grams and the amount of toluene removed was 25.07 grams. The batch was agitated at 92.9°–94.0° C. for 15 minutes and cooled to 75° C. in 75 minutes. It was then held at 75° C. for 30 minutes. Solids in the slurry settled well throughout the 30-minute 75° C. ride. A total of 1840 grams of 75° C. toluene was used to rinse the reactor and to wash the wet centrifuge cake (sodium (S)-2-(6-methoxy-2-naphthyl)propionate monohydrate). Totals of 6224.1 and 1225.15 grams of mother liquor and wash liquor were recovered, respectively. An undetermined amount of product remained in the reactor and was not accounted for in the calculations of yields. The wet centrifuge cake weighed 994.74 grams which after drying for 4 hours at ambient temperature and under full vacuum yielded 959.89 grams of product. The product was dried further for 12 hours at 80°–90° C. and under full vacuum. A total of 892.57 grams of dry final product (anhydrous sodium (S)-2-(6-methoxy-2-naphthyl)propionate) was obtained. Chiral purities for the product and the mother liquor were found by analysis to be 99.28% S-enantiomer and 81.40% S-enantiomer, respectively.

EXAMPLE 8

Using the apparatus of the above Comparative Example, a toluene solution of 2-(6-methoxy-2-naphthyl)propionic acid (580.68 grams, 18.11 wt % solids, 91.64% S-enantiomer) was prepared from a sample of high chiral purity (S)-2-(6-methoxy-2-naphthyl)propionic acid, and racemic 2-(6-methoxy-2-naphthyl)propionic acid. The solution was heated to 85° C. Totals of 27.59 grams of 49.22 wt % NaOH and 7.822 grams of water were added. Two clear liquid phases were obtained. Water was stripped to 94.0° C. in 285 minutes. The total amount of water collected during the strip was 21.36 grams and the amount of toluene removed was 1.83 grams. The batch was agitated at 93.6°–94.0° C. for 15 minutes and cooled to 75° C. in 82 minutes and agitated at 75° C. for 60 minutes. Solids in the slurry settled well at the end of the 60-minute 75° C. ride. The centrifuge cake (sodium (S)-2-(6-methoxy-2-naphthyl) propionate monohydrate) was washed with 149.94 grams of hot (75° C.) toluene. Totals of 483.77 and 127.61 grams of mother liquor and wash liquor were recovered, respectively. The wet centrifuge cake weighed 75.02 grams which after drying for 8 hours at 80°–90° C. and under full vacuum yielded 67.29 grams of anhydrous sodium (S)-2-(6-methoxy-2-naphthyl)propionate. Chiral purities for the product and the mother liquor were found by analysis to be 99.03% S-enantiomer and 80.28% S-enantiomer, respectively.

EXAMPLE 9 AND COMPARATIVE EXAMPLE B

The following were charged to the same reactor setup as in the above Comparative Example A: 97.66 grams of 2-(6-methoxy-2-naphthyl)propionic acid assaying 98.90%

S-enantiomer, 4.46 grams of racemic 2-(6-methoxy-2-naphthyl)propionic acid, 458.72 grams of fresh toluene, and 1.62 grams of water. The mixture was heated to 85° C. to dissolve the solids. The composite solution was analyzed for chiral purity (result: 96.71% S-enantiomer). A total of 31.93 grams of 49.99 wt % NaOH was then added. Also added was 16.119 grams of water. Two clear liquid phases were obtained. Water was stripped to 94.1° C. in 323 minutes. After about 4 minutes ride at 94° C., a sample of the slurry was drawn, filtered and the solids (sodium (S)-2-(6-methoxy-2-naphthyl)propionate monohydrate) were washed with 85° C. toluene. The reactor slurry contained very large crystals. The water strip was resumed and continued until the pot temperature reached 100° C. When the temperature was 94.2° C., the slurry began thickening. A temperature drop (to 93.6° C.) was observed. This portion of the strip was 102 minutes. The total amount of water collected during the entire strip was 37.57 grams and the amount of toluene removed was 11.90 grams. The batch was agitated at 100° C. for 15 minutes and cooled to 65° C. in 89 minutes and then held there for 30 minutes. The final slurry was very thick. It was then centrifuged and the centrifuge cake was washed with 201.56 grams of warm (65° C.) toluene. Totals of 398.44 and 154.74 grams of mother liquor and wash liquor were recovered, respectively. The wet centrifuge cake weighed 100.84 grams which after drying for 8 hours at 80°–90° C. and under full vacuum yielded 90.75 grams of dry product. Chiral purities for the final product and the mother liquor were found by analysis to be 98.48% S-enantiomer and 87.73% S-enantiomer, respectively. Chiral purity of the crystals (anhydrous sodium (S)-2-(6-methoxy-2-naphthyl)propionate) isolated from the slurry at 94° C. was 99.49% S-enantiomer, whereas the chiral purity of the corresponding mother liquor was 86.80% S-enantiomer. (Note: The operation up to the withdrawal of the sample after the strip to 94.1° C. illustrates practice of the invention, whereas the remainder of the operation was for comparative purposes.)

EXAMPLE 10

The following were charged to a thick-walled 1000-mL glass reactor: 97.52 grams of naproxen of 99.7% chiral purity, 6.52 grams of racemic naproxen, 465.92 grams of fresh toluene, 36.96 grams of water, and 16.06 grams of solid sodium hydroxide. The reactor was equipped with a mechanical agitator and a stainless steel condenser which was cooled with tap water. The condenser was fitted with a receiver which had a regulator to maintain the back pressure at 135.8 kPa (5 psig) with nitrogen gas. The mixture was heated to 85° C. to dissolve all solids. Two clear liquid phases were obtained. Water was stripped to 100.0° C. in 503 minutes. No toluene was refluxed back to the reactor. The total amount of water collected during the strip was 33.61 grams and the amount of toluene removed was 130.93 grams. The batch was cooled to 70° C. in 142 minutes. It was then centrifuged and the centrifuge cake was washed with about 200 grams of warm (70° C.) toluene. Totals of 295.52 and 133.44 grams of mother liquor and wash liquor, respectively, were recovered. The wet centrifuge cake weighed 99.42 grams which after drying for 8 hours at ambient temperature and under full vacuum yielded 91.65 grams of dry product. The chiral purity of the product was determined to be 99.10% (S)-enantiomer. The average particle size of the product was determined to be 130 microns.

The products formed in Examples 1–10 were all compositions of this invention in that each before dehydration was sodium (S)-2-(6-methoxy-2-naphthyl)propionate monohydrate having an average particle size of at least about 120 microns, and a chiral purity of at least 98% (S)-enantiomer, and each after dehydration was anhydrous sodium (S)-2-(6-methoxy-2-naphthyl)propionate having an average particle size of at least about 120 microns, and a chiral purity of at least 98% (S)-enantiomer. Table 1 summarizes some of the conditions and results of the Examples wherein detailed particle size measurements were made.

TABLE 1

| Example | Starting Acid Chiral Purity, % (S) Form | NaOH/Starting Acid, mole/mole | Final Strip Temp., °C. | Product Chiral Purity, % (S)-Form | Average Particle Size, Microns |
| --- | --- | --- | --- | --- | --- |
| Comp. A | 97.99 | 0.900 | 100.0 | 98.96 | 84 |
| 1 | 96.80 | 0.903 | 94.3 | 98.85 | 145 |
| 2 | 96.80 | 0.893 | 94.1 | 99.53 | 357 |
| 7 | 91.95 | 0.750 | 94.0 | 99.28 | 282 |
| 9 | 96.71 | 0.900 | 94.1 | — | ca. 350* |
| Comp. B | 96.71 | 0.900 | 101.0 | 98.48 | 54 |

*Average particle size of this sample was not measured but visually it had crystals as large as those of Example 2.

It is to be understood that the components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what preliminary chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. Sodium (S)-2-(6-methoxy-2-naphthyl)propionate monohydrate having an average particle size of at least about 120 microns, and a chiral purity of at least 98% (S)-enantiomer.

2. Sodium (S)-2-(6-methoxy-2-naphthyl)propionate monohydrate in accordance with claim 1 wherein said chiral purity is at least 99%.

3. Sodium (S)-2-(6-methoxy-2-naphthyl)propionate monohydrate in accordance with claim 1 wherein said average particle size is at least about 250 microns.

4. Sodium (S)-2-(6-methoxy-2-naphthyl)propionate monohydrate in accordance with claim 3 wherein said chiral purity is at least 99%.

5. Sodium (S)-2-(6-methoxy-2-naphthyl)propionate monohydrate in accordance with claim 1 wherein said average particle size is at least about 330 microns.

6. Sodium (S)-2-(6-methoxy-2-naphthyl)propionate monohydrate in accordance with claim 5 wherein said chiral purity is at least 99%.

7. A process which comprises:
   a) forming a solids-free mixture from (i) (S)-2-(6-methoxy-2-naphthyl)propionic acid having a chiral purity of at least about 82%, but below 99%, (ii) water, (iii) at least one water-soluble inorganic basic sodium compound in an amount proportioned to neutralize from about 50 to about 97% of said acid, and (iv) an inert organic solvent; and
   b) removing water from said mixture by distillation such that a pot residue containing sodium (S)-2-(6-methoxy-2-naphthyl)propionate monohydrate having an average particle size of at least about 120 microns, and a chiral purity of at least 98% (S)-enantiomer is formed.

8. A process according to claim 7 wherein said organic solvent used is a hydrocarbon solvent.

9. A process according to claim 7 wherein said organic solvent used is a solvent that can form an azeotrope with water that boils below 100° C. at ambient pressure.

10. A process according to claim 9 wherein said organic solvent used is a hydrocarbon solvent.

11. A process according to claim 7 wherein at least a portion of said sodium compound is added as a water solution.

12. A process according to claim 7 wherein said sodium compound used is sodium hydroxide and/or sodium oxide.

13. A process according to claim 12 wherein at least a portion of said sodium hydroxide and/or sodium oxide is added as a water solution.

14. A process according to claim 7 wherein said (S)-2-(6-methoxy-2-naphthyl)propionic acid has a chiral purity of at least about 82%, but below 98%.

15. A process according to claim 7 wherein said organic solvent used is a hydrocarbon solvent; wherein at least a portion of said sodium compound is added as a water solution; and wherein said (S)-2-(6-methoxy-2-naphthyl) propionic acid has a chiral purity of at least about 82%, but below 98%.

16. A process according to claim 15 wherein said hydrocarbon solvent used is a hydrocarbon solvent that can form an azeotrope with water that boils below 100° C. at ambient pressure.

17. A process according to claim 15 wherein said sodium compound used is sodium hydroxide, sodium oxide, sodium carbonate and/or sodium bicarbonate.

18. Anhydrous sodium (S)-2-(6-methoxy-2-naphthyl) propionate having an average particle size of at least about 120 microns, and a chiral purity of at least 98% (S)-enantiomer.

19. Anhydrous sodium (S)-2-(6-methoxy-2-naphthyl) propionate in accordance with claim 18 wherein said chiral purity is at least 99%.

20. Anhydrous sodium (S)-2-(6-methoxy-2-naphthyl) propionate in accordance with claim 18 wherein said average particle size is at least about 250 microns.

21. Anhydrous sodium (S)-2-(6-methoxy-2-naphthyl) propionate in accordance with claim 20 wherein said chiral purity is at least 99%.

22. Anhydrous sodium (S)-2-(6-methoxy-2-naphthyl) propionate in accordance with claim 18 wherein said average particle size is at least about 330 microns.

23. Anhydrous sodium (S)-2-(6-methoxy-2-naphthyl) propionate in accordance with claim 22 wherein said chiral purity is at least 99%.

24. A process which comprises dehydrating particulate sodium (S)-2-(6-methoxy-2-naphthyl)propionate monohydrate having an average particle size of at least about 120 microns, and a chiral purity of at least 98% (S)-enantiomer under conditions effective to form, and so that there is formed, particulate anhydrous sodium (S)-2-(6-methoxy-2-naphthyl)propionate having an average particle size of at least about 120 microns, and a chiral purity of at least 98% (S)-enantiomer.

25. A process according to claim 24 wherein said monohydrate and said anhydrous sodium (S)-2-(6-methoxy-2-naphthyl)propionate both have a chiral purity of at least 99%.

26. A process according to claim 24 wherein said monohydrate and said anhydrous sodium (S)-2-(6-methoxy-2-naphthyl)propionate both have an average particle size of at least about 250 microns.

27. A process according to claim 26 wherein said monohydrate and said anhydrous sodium (S)-2-(6-methoxy-2-naphthyl)propionate both have a chiral purity of at least 99%.

28. A process according to claim 24 wherein said monohydrate and said anhydrous sodium (S)-2-(6-methoxy-2-naphthyl)propionate both have an average particle size of at least about 330 microns.

29. A process according to claim 28 wherein said monohydrate and said anhydrous sodium (S)-2-(6-methoxy-2-naphthyl)propionate both have a chiral purity of at least 99%.

* * * * *